United States Patent
Botár et al.

(10) Patent No.: US 10,968,224 B2
(45) Date of Patent: Apr. 6, 2021

(54) 2,11-DIAZA-[3.3](2,6)PYRIDINOPHANE COMPOUNDS AND THEIR APPLICATION AS LIGANDS OF ESSENTIAL METAL ION BASED MRI CONTRAST AGENTS AND 52MN BASED PET CONTRAST AGENTS

(71) Applicant: DEBRECENI EGYETEM, Debrecen (HU)

(72) Inventors: Richárd Botár, Emöd (HU); Zoltán Garda, Túrricse (HU); Tamás Fodor, Miskolc (HU); Ferenc Krisztián Kálmán, Debrecen (HU); Viktória Nagy, Debrecen (HU); Gyula Tircsó, Debrecen (HU); Imre Tóth, Debrecen (HU)

(73) Assignee: DEBRECENI EGYETEM, Debrecen (HU)

( * ) Notice: Subject to any disclaimer, the term of this patent is extended or adjusted under 35 U.S.C. 154(b) by 126 days.

(21) Appl. No.: 15/778,489

(22) PCT Filed: Nov. 25, 2016

(86) PCT No.: PCT/HU2016/000074
§ 371 (c)(1),
(2) Date: May 23, 2018

(87) PCT Pub. No.: WO2017/089848
PCT Pub. Date: Jun. 1, 2017

(65) Prior Publication Data
US 2018/0282333 A1    Oct. 4, 2018

(30) Foreign Application Priority Data

Nov. 26, 2015  (HU) .................................. P1500565
Oct. 18, 2016  (HU) .................................. P1600582

(51) Int. Cl.
*A61K 51/00*  (2006.01)
*A61M 36/14*  (2006.01)
(Continued)

(52) U.S. Cl.
CPC ........ *C07D 471/18* (2013.01); *A61K 51/0472* (2013.01); *A61K 51/0482* (2013.01); *A61K 2123/00* (2013.01)

(58) Field of Classification Search
None
See application file for complete search history.

(56) References Cited

U.S. PATENT DOCUMENTS 5,316,756 A   5/1994  Gries et al.
5,334,371 A   8/1994  Gries et al.
(Continued)

FOREIGN PATENT DOCUMENTS

EP    0 130 934    1/1985
EP    0 263 059    4/1988
(Continued)

OTHER PUBLICATIONS

Choppin et al. (Inorganica Chimica Acta 1996, 252, 299-310).*
(Continued)

*Primary Examiner* — Michael G. Hartley
*Assistant Examiner* — Melissa J Perreira
(74) *Attorney, Agent, or Firm* — Smith, Gambrell & Russell, LLP

(57) ABSTRACT

The one subject of the invention is the compounds of general formula (I), their isomers, their physiologically acceptable salts and/or Mn(II), Fe(II), Fe(III), Co(II) and Ni(II) complexes. The other subject of the invention is the application of the above compounds. The compounds of general formula (I): wherein —NRR$_1$ group may refer to: a) —NRR$_1$ with N atom in the ring means a ring of 4 to 7, that in certain cases may contain another heteroatom, and in specific cases the ring may be replaced with an aryl group (of 5 to 7 carbon atoms) substituted with —COOH, —OH, —OCH$_3$, —NO$_2$, —NH$_2$, —NCS, —NHS-activated ester, aryl (of 5 to 7 carbon atoms), or nitro-, amino- or isothiocyanate group, or b) in the —NRR$_1$ group R means a H atom, alkyl, aryl, nitroaryl, aminoaryl or isothiocyanate-aryl group (of 1 to 6 carbon atoms) and R$_4$ is a H atom, alkyl (of 1 to 6 carbon atoms) or —(CH$_2$)$_n$—COOH group, whereas n=1 to 10 integer, or c) —NRR$_1$ group is one of the following groups: (formula II) whereas R$_2$ is a H atom, carboxyl- or alkyl-carbonyl group (of 1 to 4 carbon atoms); (formula III) and R$_2$ is a H atom or alkyl or aryl group (of 1 to 6 carbon atoms), and X means independently from one another H atom, —CH$_3$, —COOH, —OH, —OCH$_3$, alkoxy- (of 2 to 6 carbon atoms), —NO$_2$, —NH$_2$, —NCS, —NHS-activated ester, alkyl (of 2 to 12 carbon atoms) or aryl (of 5 to 7 carbon atoms) group, in certain cases the latter may be substituted with hydroxyl, hydroxyalkyl (of 1 to 6 carbon atoms), nitro, amino or isothiocyanate group.

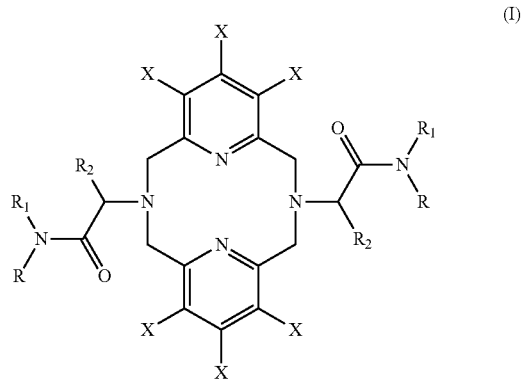

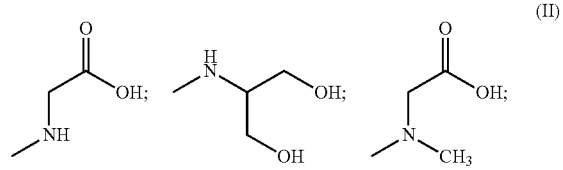

(Continued)

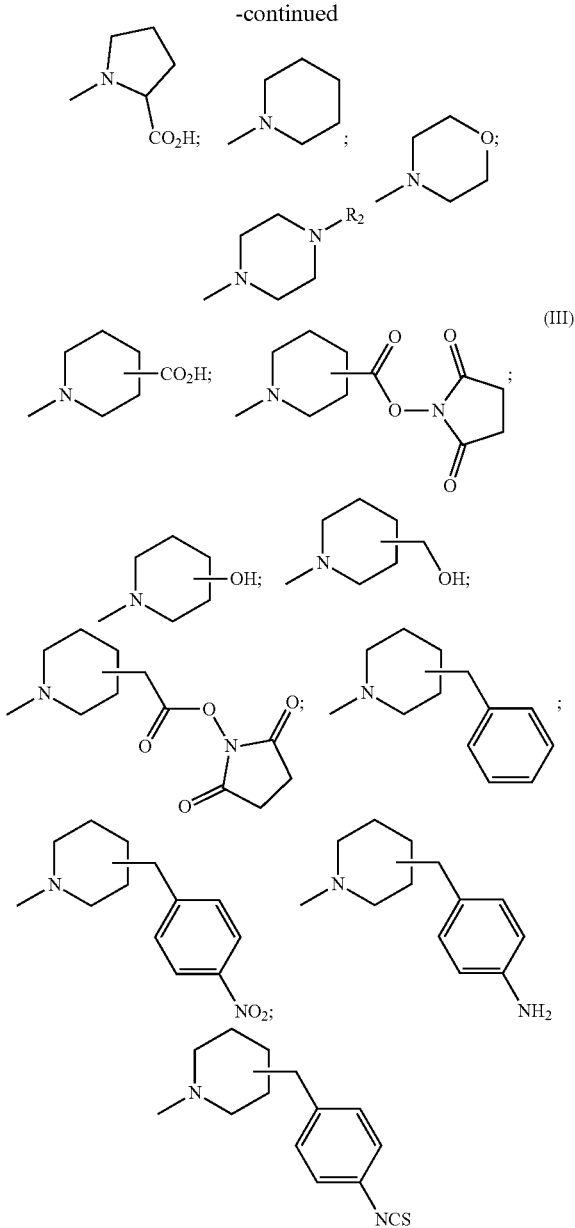

6 Claims, No Drawings

(51) Int. Cl.
 C07D 471/18 (2006.01)
 A61K 51/04 (2006.01)

(56) References Cited

U.S. PATENT DOCUMENTS

| | | | | |
|---|---|---|---|---|
| 5,385,893 | A * | 1/1995 | Kiefer | C07D 471/18 424/9.363 |
| 5,480,990 | A | 1/1996 | Kiefer et al. | |
| 5,693,310 | A | 12/1997 | Gries et al. | |
| 8,268,810 | B2 | 9/2012 | Port | |
| 9,107,948 | B2 * | 8/2015 | Ballet | A61K 49/1866 |
| 2010/0092396 | A1 | 4/2010 | Kovacs et al. | |
| 2011/0092806 | A1 | 4/2011 | Port et al. | |
| 2014/0206862 | A1 | 7/2014 | Green et al. | |
| 2015/0209452 | A1 | 7/2015 | Mirica et al. | |
| 2018/0344883 | A1 | 12/2018 | Botar et al. | |
| 2018/0354969 | A1 | 12/2018 | Botar et al. | |

FOREIGN PATENT DOCUMENTS

| | | |
|---|---|---|
| WO | 90/11282 | 10/1990 |
| WO | 94/26276 | 11/1994 |
| WO | 99/65905 | 12/1999 |
| WO | 2011/073371 | 6/2011 |

OTHER PUBLICATIONS

Castro et al. (Inorg. Chem. 2015, 54, 1671-1683).*
Rojas-Quijano et al. (Chem. Eur. J. 2009, 15, 13188-13200).*
Weber, E., et al. Ligandstruktur and Komplexierung, V[1)] Neue Kronenäther und ihre Alkalimetailion-Komplexe. [Ligand Structure and Complexation, V[1)] New Crown Ethers and Their Alkali Metal Ion Complexes]. Chemische Berichte, 1976. vol. 109, No. 5, pp. 1803-1831 (with partial English translation).
Aime, S. et al. Designing Novel Contrast Agents for Magnetic Resonance Imaging. Synthesis and Relaxonaetric Characterization of three Gadolinium(III) Complexes Based on Functionalized Pyridine-Containing Macrocyclic Ligands. Helvetica Chimica Acta. 2003. vol. 86, pp. 615-632.
Kim, W.D., et al. Synthesis, Crystal Structure, and Potentiometry of Pyridine-Containing Tetraaza Macrocyclic Ligands with Acetate Pendant Arms. Inorganic Chemistry, 1995. vol. 34, pp. 2225-2232.
Rojas-Quijano, F.A., et al. Lathanide(III) Complexes of Tris(amide) PCTA Derivatives as Potential Bimodal Magnetic Resonance and Optical Imaging Agents. Chemistry—A European Journal. 2009. vol. 15, pp. 13188-13200.
Oschepkov, M.S., et al. Synthesis of Azaerown Ethers and Berizocryptands by Macrocyclization of Podands at High Concentrations of Reactants. Russian Chemical Bulletin, International Edition. 2011. vol. 60, No. 3, pp. 478-485.
International Search Report mailed relative to PCT/HU2016/000074, dated Feb. 10, 2017 (4 pages).
Written Opinion of the International Searching Authority, mailed relative to PCT/HU2016/000074, dated Feb. 10, 2017 (6 pages).
International Search Report mailed relative to PCT/HU2016/000073, dated Apr. 5, 2017 (5 pages).
Written Opinion of the International Searching Authority, mailed relative to PCT/HU2016/000073, dated Apr. 5, 2017 (8 pages).
International Search Report mailed relative to PCT/HU2016/000075, dated Feb. 6, 2017 (5 pages).
Written Opinion of the International Searching Authority, mailed relative to PCT/HU2016/000075, dated Feb. 6, 2017 (6 pages).
EMA's final opinion confirms restrictions on use of linear gadolinium agents in body scans, *European Medicines Agency Science Medicines Health*, EMA/625317/2017 pp. 1-4 (Nov. 23, 2017).
Liu et al., "Structural Characterization and Relaxivity Study of a New Paramagnetic Mn(II) Complex of DTPA-BpABA," *Chinese Journal of Chemistry* 23 1012-1016 (2005).
Tei, et al., "Mn(II) complexes of novel hexadentate AAZTA-like chelators: a solution thermodynamics and relaxometric study," *Dalton Transaction.*, 40(9), 2025-2032 (2011).
Zhen-Chuan et al., "Synthesis and Evaluation of Neutral Gd(III), Mn(II) Complexes From DTPA-Bisamide Derivative as Potential MRI Contrast Agents," *Journal Homepage* http://www/tandonline.com/loi/lsrt20 ISSN: 1553-3174 (2015).
Zoltán et al., "Effect of the Nature of Donor Atoms on the Thermodynamic, Kinetic and Relaxation Properties of Mn(II) Complexes Formed With Some Trisubstituted 12-Membered Macrocyclic Ligands," *Frontiers in Chemistry* pp. 1-14 (2018).
Zoltán et al., "Physico-chemical properties of $Mn^{II}$ complexes formed with cis-and trans-DO2A: thermodynamic, electrochemical

(56) References Cited

OTHER PUBLICATIONS and kinetic studies," *Journal of Inorganic Biochemistry* 163 pp. 206-213 (2016).

* cited by examiner

2,11-DIAZA-[3.3](2,6)PYRIDINOPHANE COMPOUNDS AND THEIR APPLICATION AS LIGANDS OF ESSENTIAL METAL ION BASED MRI CONTRAST AGENTS AND 52MN BASED PET CONTRAST AGENTS

Subject of the invention is new substituted 2,11-diaza-[3.3](2,6)pyridinophane derivatives and their application as ligand in Mn(II), Fe(II), Fe(III), Co(II) and Ni(II) as MRI contrast agents.

They are applied as well in $^{52}$Mn based Positron Emission Tomography (PET).

The invention is referring to the new compounds and their applications of the general formula (I)

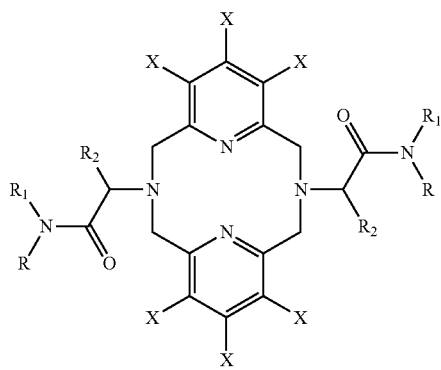

(I)

wherein
—NRR$_1$ group may represent:

a) —NRR$_1$ with N atom in the ring means a ring of 4 to 7, that in certain cases may contain another heteroatom, and in specific cases the ring may be replaced with an aryl group (of 5 to 7 carbon atoms) substituted with —COOH, —OH, —OCH$_3$, —NO$_2$, —NH$_2$, —NCS, —NHS-activated ester, aryl (of 5 to 7 carbon atoms), or nitro-, amino- or isothiocyanate group, or b) in the —NRR$_1$ group R means a H atom, alkyl, aryl, nitroaryl, aminoaryl or isothiocyanate-aryl group (of 1 to 6 carbon atoms) and R$_4$ is a H atom, alkyl (of 1 to 6 carbon atoms) or —(CH$_2$)—COOH group, whereas n=1 to 10 integer, or c) —NRR$_1$ group is one of the following groups:

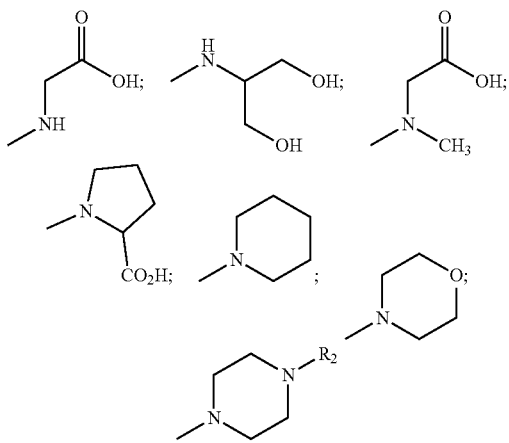

whereas R$_2$ is a H atom, carboxyl- or alkyl-carbonyl group (of 1 to 4 carbon atoms);

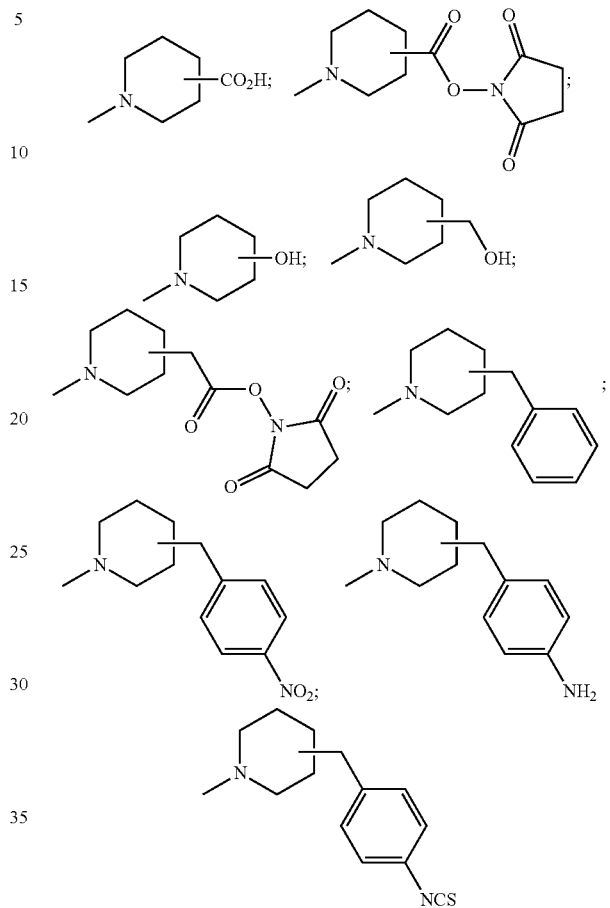

and

R$_2$ is a H atom or alkyl or aryl group (of 1 to 6 carbon atoms), and

X means independently from one another H atom, —CH$_3$, —COOH, —OH, —OCH$_3$, alkoxy- (of 2 to 6 carbon atoms), —NO$_2$, —NH$_2$, —NCS, —NHS-activated ester, alkyl (of 2 to 12 carbon atoms) or aryl (of 5 to 7 carbon atoms) group, in certain cases the latter may be substituted with hydroxyl, hydroxyalkyl (of 1 to 6 carbon atoms), nitro, amino or isothiocyanate group;

Mn(II), Fe(II), Fe(III), Co(II), and Ni(II) complexes of compounds with (I) general formula can be applied beneficially in MRI and $^{52}$Mn based PET diagnostics as contrast agents.

The majority of contrast agents applied in MRI diagnostics are complexes of paramagnetic Gd(III) ion with different ligands. An important disadvantage of Gd(III) containing contrast agents is the toxicity of Gd(III) ion, therefore very strict requirements shall be fulfilled for their application as contrast agent. Nephrogenic Systemic Fibrosis (NSF) discovered in the beginning of the 21$^{st}$ Century and associated with the use of Gd(III) containing contrast agents in patients with severe renal disease pointed out that problems may arise due to the use of toxic Gd(III) even in spite of the strict requirement system. Furthermore, the negative outcome of using high quantities of Gd(III) based contrast agents, e.g.

gadolinium accumulating in surface waters and coming from clinical waste waters also poses an increasing problem.

The only contrast agent without Gd(III) used in practice was Mangafodipir (Tesalscan) with Mn(II) ion as the central paramagnetic ion, but this was withdrawn from the European market some years ago.

One possibility to decrease the toxicity of the agents is to replace Gd(III) by an essential paramagnetic (such as Mn(II), Fe(II), Fe(III)) metal ion in the contrast agents. Since Mn(II) ion is an essential metal ion, thus appropriate routes for elimination of Mn(II) ion are available in living organisms. Mangafodipir mentioned above can be applied in liver diagnostics due to the different Mn(II) uptake of the healthy and abnormal hepatocytes. In case of Mangafodipir contrast agent, the Mn(II) ions released after dissociation of the complex are taken up possibly due to low kinetic inertness of the complex. At the same time, however, publications are available to support, that despite the endogenic nature of the Mn(II) ion, extended expositions and high doses may cause neurodegenerative changes with Parkinson-like symptoms. Therefore it is more safe to use Mn(II), Fe(II), Fe(III) ion containing contrast agents (complexes) not dissociating or dissociating only at a very small extent while the complex is excreted form the body. The kinetic inertness of Co(II) and Ni(II) ion based contrast agents are also important for very similar reasons.

During the research of Mn(II) ion based Magnetic Resonance Imaging (MRI) contrast agent, synthesis of a macrocycle based complexes applicable as contrast agents in MRI have not been succeeded yet. It is obviously due to the small contrast enhancement effect of complexes caused by the lack of water molecule bound directly to the metal ion. To solve this problem, we managed to design and synthesis macrocyclic ligands, the Mn(II) complexes of which preserve the good equilibrium and kinetic properties, while their relaxation properties fulfil the requirements related to MRI contrast agents (e.g. water molecule is present in the internal coordination sphere).

Together with other documents, the published EP 130934 document describes Mn(II) ion containing contrast agents and substituted tetraacetic-acid-bis(amide) type ligands suitable for the preparation of the mentioned contrast agents, describing trans-1,2-cyclohexanediamine-tetraacetic acid (CDTA)-bis(amide) derivatives and their Mn(II), Fe(II), Fe(III), Co(II), and Ni(II) complexes.

The published EP 263059 document provides additional similar compounds as derivatives of the trans-1,2-cyclohexanediamine-tetraacetic acid-bismethyl-amide and bis(3-oxa-pentamethylene)-carboxamide.

The published US 2011/0092806 document describes 'chelate-linker-biovector' type associates for application in diagnostic imaging having DPTA, DOTA, NOTA, DO3A and PCTA basic structure or their derivatives.

The WO 2011/073371 international publication refers to substituted 3,6,9,15-tetraazabicyclo[9.3.1]pentadecatriene derivatives and the Mn(II) complexes of the same carrying acetic acid ester group on the basic structure.

In our research, the main goal was to develop Mn(II), Fe(II), Fe(III), Co(II) and Ni(II) ion based complexes of high relaxivity and high kinetic inertness for their application as contrast agents in MRI as well as $^{52}$Mn based PET.

In our experiments, the 2,11-di-aza-[3.3](2,6)pyridinophane macrocyclic compounds with general formula (I) were found favourable as complex forming agents of new type contrast agents.

Synthesis of compounds of the invention is shown in the following examples:

EXAMPLE 1

Synthesis of BP2AM$^{Pyp}$ a.) 2-bromo-1-(piperidine-1-yl)ethanone

Bromoacetyl bromide (3.56 g, 17.6 mmol, 1.55 ml, 1.5 equivalent), dry $CH_2Cl_2$ (50 ml) and $K_3PO_4$ (6.41 g, 30.2 mmol, 2.5 equ.) was mixed in a flask of 250 ml under $N_2$ atmosphere. Piperidine (1.00 g, 11.7 mmol, 1.0 equivalent) was dissolved in dry $CH_2Cl_2$ (20 ml) and was added dropwise to dichloromethane solution of bromoacetyl bromide at 0° C. in 30 minutes, then the reaction mixture was stirred for additional 12 hours at room temperature under $N_2$ atmosphere before the aqueous HCl solution (0.5 M, 30 ml) was added to the reaction mixture. After the addition of HCl solution, the reaction mixture was stirred for additional 5 minutes, then the two phases were separated using a separatory funnel. The aqueous phase was washed with $CH_2Cl_2$ (1×15 ml) and then the unified organic phases were washed with $KHCO_3$ solution (2×30 ml, 10 m/m %) and saturated NaCl solution (1×30 ml). The organic phase was dried with $MgSO_4$, then dichloromethane was evaporated at reduced pressure, and the crude product was stored at −20° C. until further use. Yield: 1.73 g (70%).

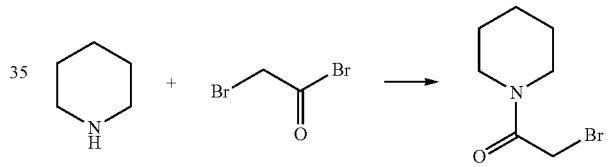

$^1$H NMR [360 MHz, $CDCl_3$] δ 1.59 (2H, m, ($CH_2$) ring), 1.67 (4H, m, ($CH_2$) ring), 3.45 (2H, t, ($CH_2$) ring), 3.59 (2H, t, ($CH_2$) ring), 3.87 (2H, s, ($CH_2$)), $^{13}$C NMR [100 MHz, $CDCl_3$] δ 25.4 (2 pcs $CH_2$ ring); 26.0 ($CH_2$ ring); 27.2 ($CH_2Br$); 44.2 (2 pcs $CH_2$ ring); 169.5 (C(=O));

b.) Synthesis of BP2AM$^{Pyp}$

The 2-bromo-1-(piperidin-1-yl)ethanone obtained as described above (0.22 g, 1.05 mmol, 2.5 equivalent) was dissolved in dry acetonitrile and added dropwise to the acetonitrile solution (30 ml) of 2,11-diaza[3.3](2,6)-pyridinophane (0.10 g, 0.42 mmol, 1 equivalent) obtained form commercial sources and $K_2CO_3$ (0.17 g, 1.26 mmol, 3 equivalent) at room temperature within 30 minutes. Then the reaction mixture was refluxed in $N_2$ atmosphere for 24 hours. After 24 hours, $K_2CO_3$ was filtered from the hot solution, and acetonitrile was evaporated at reduced pressure. The obtained crude product was purified with HPLC (Luna 10u-Prep C18(2) 100A (250×21.20 mm; 10 μm) column), ACN:$H_2O$/TFA was applied as eluent [ACN: acetonitrile; TFA: trifluoroacetic acid]. TFA was contained only in water in 0.005 M concentration. The received compound is 2,11-bis[2-oxo-2-(piperidine-1-il)-ethyl]-2,11-diaza[3.3](2,6)-pyridinophane. Yield: 0.11 g (52%)

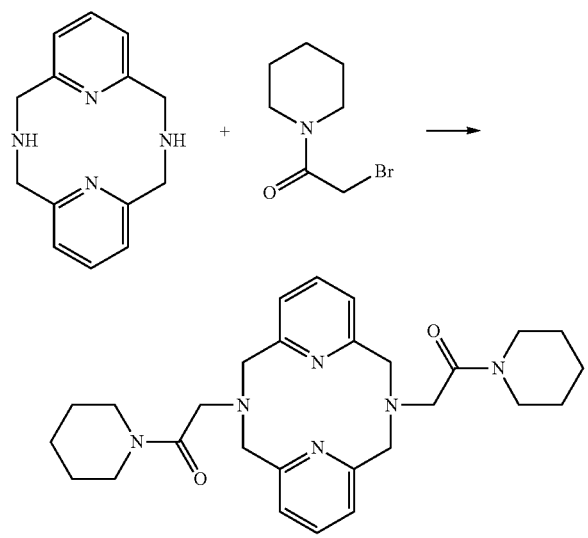

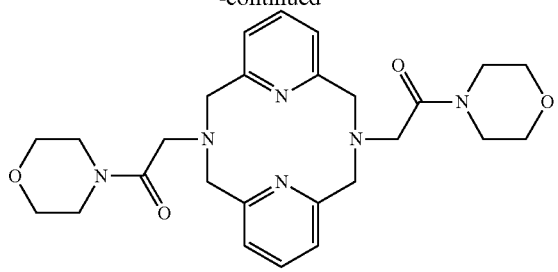

¹H NMR [360 MHz, D₂O] δ 3.35 (4H, s, (2 pcs CH₂)), 3.51-3.71 (16H, m, (8 pcs CH₂)), 4.33 (8H, br, (4 pcs CH₂)), 7.18 (4H, d, (4 pcs CH) aromatic), 7.74 (2H, t, (2 pcs CH) aromatic); ¹³C NMR [100 MHz, D₂O] δ 45.5 (4 pcs CH₂); 56.1 (2 pcs CH₂); 59.9 (4 pcs CH₂); 69.1 (4 pcs CH₂); 123.7 (4 pcs CH aromatic); 133.4 (2 pcs CH aromatic); 150.2 (4 pcs C aromatic); 166.1 (2 pcs C(=O)

EXAMPLE 3

Synthesis of BP2AMP$^{PipAc}$

The commercially available 1-acetyl-4-(bromoacetyl) piperazine (0.265 g, 1.06 mmol, 2.5 equivalent) was dissolved in dry acetonitrile (5 ml), then added dropwise to the acetonitrile suspension (30 ml) of 2,11-diaza[3.3](2,6)-pyridinophane (0.10 g, 0.42 mmol, 1 equivalent) and K₂CO₃ (0.17 g, 1.26 mmol, 3 equivalent) at room temperature within 30 minutes. Then the reaction mixture was refluxed in N₂ atmosphere for 24 hours. After 24 hours, K₂CO₃ was filtered from the hot solution, and the filtrate was evaporated at reduced pressure. The obtained crude product was purified with HPLC (Luna 10u-Prep C18(2) 100A (250×21.20 mm; 10 μm) column), ACN:H₂O/TFA was applied as eluent [ACN: acetonitrile; TFA: trifluoroacetic acid]. TFA was contained only in water in 0.005 M concentration. Yield: 0.13 g (54%).

¹H NMR [360 MHz, D₂O] δ 1.30-1.55 (12H, m, (6 pcs CH₂)), 3.30 (4H, t, (2 pcs CH₂)), 3.4 (4H, t, (2 pcs CH₂)), 4.59 (8H, s, (4 pcs CH₂)), 4.84 (4H, s, (2 pcs CH₂)), 7.08 (4H, d, (4 pcs CH) aromatic), 7.56 (1H, t, (2 pcs CH) aromatic);
¹³C NMR [100 MHz, D₂O] δ 23.4 (2 pcs CH₂); 24.9 (2 pcs CH₂); 25.5 (2 pcs CH₂); 43.7 (4 pcs CH₂); 45.6 (2 pcs CH₂); 58.5 (2 pcs CH₂); 60.8 (2 pcs CH₂); 124.1 (4 pcs CH aromatic); 140.5 (2 pcs CH aromatic); 149.6 (4 pcs C aromatic); 164.0 (2 pcs C(=O));
MS (ESI) m/z 491.500 (M+H)⁺ 100%; 513.500 (M+Na)⁺ 10%;
IR: 1624 cm⁻¹ (>C=O); 2164, 2024 (aromatic >C=C) és 1093 cm⁻¹ (≥C—O—C≤);

EXAMPLE 2

Synthesis of BP2AM$^{Morf}$

The commercially available 4-(bromoacetyl)morpholine (0.22 g, 1.06 mmol, 2.5 equivalent) was dissolved in dry acetonitrile (5 ml), then added dropwise to the acetonitrile suspension (30 ml) of 2,11-diaza[3.3](2,6)-pyridinophane (0.10 g, 0.42 mmol, 1 equivalent) and K₂CO₃ (0.17 g, 1.26 mmol, 3 equivalent) at room temperature within 30 minutes. Then the reaction mixture was refluxed in N₂ atmosphere for 24 hours. After 24 hours, K₂CO₃ was filtered from the hot solution, and the solvent was evaporated at reduced pressure. The obtained crude product was purified with HPLC (Luna 10u-Prep C18(2) 100A (250×21.20 mm; 10 μm) column), ACN:H₂O/TFA was applied as eluent [ACN: acetonitrile; TFA: trifluoroacetic acid]. TFA was contained only in water in 0.005 M concentration. Yield: 0.09 g (43%).

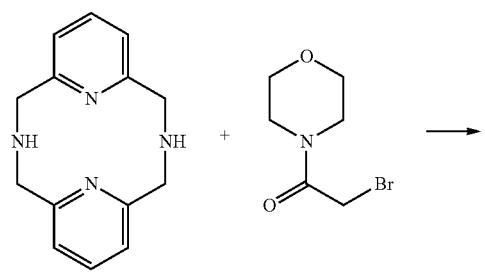

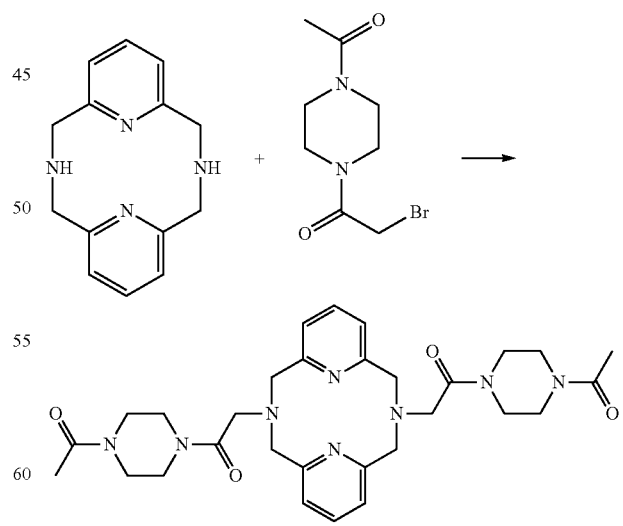

¹H NMR [360 MHz, D₂O] δ 2.23 (6H, s, 2 pcs CH₃), 3.33 (4H, s, (2 pcs CH₂)), 3.50-3.74 (16H, m, (8 pcs CH₂)), 4.29 (8H, br, (4 pcs CH₂)), 7.21 (4H, d, (4 pcs CH) aromatic), 7.77 (2H, t, (2 pcs CH) aromatic);

$^{13}$C NMR [100 MHz, D$_2$O] δ 23.5 (2 pcs CH$_3$); 54.3 (8 pcs CH$_2$); 58.8 (2 pcs CH$_2$); 65.3 (4 pcs CH$_2$); 124.4 (4 pcs CH aromatic); 131.7 (2 pcs CH aromatic); 151.1 (4 pcs C aromatic); 167.8 (2 pcs C(=O)); 173.3 (2 pcs C(=O))

EXAMPLE 4

Synthesis of diOH—BP2AM$^{Pyp}$

The 2-bromo-1-(piperidine-1-yl)ethanone manufactured as per Example 1 (0.19 g, 0.93 mmol, 2.5 equivalent) was dissolved in dry acetonitrile, then added dropwise to the acetonitrile solution (30 ml) of 2,11-diaza[3.3](2,6)-pyridinophane-7,15-diol (0.10 g, 0.37 mmol, 1 equivalent) and K$_2$CO$_3$ (0.16 g, 1.11 mmol, 3 equivalent) at room temperature within 30 minutes (the diOH—BP2AM macrocycle was synthesized by using literature procedure K. M. Lincoln, P. Gonzalez, K. N. Green, US. Pat. Appl. 2014, US 20140206862 A1 20140724 patent). Then the reaction mixture was refluxed in N$_2$ atmosphere for 24 hours. After 24 hours, K$_2$CO$_3$ was filtered from the hot solution, and the mother liquor was evaporated at reduced pressure. The obtained crude product was purified with HPLC (Luna 10u-Prep C18(2) 100A (250×21.20 mm; 10 μm) column), ACN:H$_2$O/TFA was applied as eluent [ACN: acetonitrile; TFA: trifluoroacetic acid]. TFA was contained only in water in 0.005 M concentration. Yield: 0.11 g (57%).

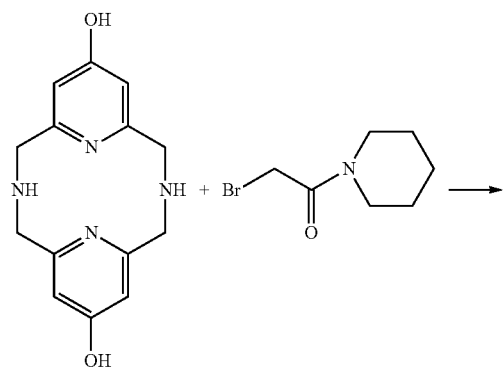

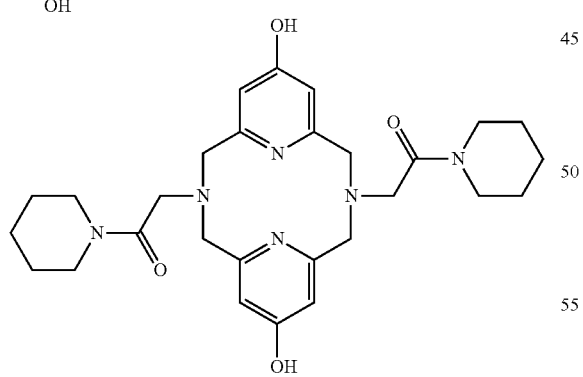

$^1$H NMR [360 MHz, D$_2$O] δ 1.54 (12H, m, (6 pcs CH$_2$)), 3.32 (4H, s, (2 pcs CH$_2$)) 3.41 (8H, m, (4 pcs CH$_2$)) 3.8-4.1 (8H, m, (4 pcs CH$_2$)), 6.41 (4H, s, (CH) aromatic);

$^{13}$C NMR [100 MHz, D$_2$O] δ 23.3 (2 pcs CH$_2$); 25.1 (2 pcs CH$_2$); 25.4 (2 pcs CH$_2$); 43.7 (4 pcs CH$_2$); 57.9 (2 pcs CH$_2$); 61.9 (4 pcs CH$_2$); 112.8 (4 pcs CH aromatic); 154.3 (2 pcs C(OH) aromatic); 157.3 (4 pcs C aromatic); 169.1 (2 pcs C(=O));

EXAMPLE 5

Synthesis of diOMe-BP2AM$^{Pyp}$

The 2-bromo-1-(piperidine-1-yl)ethanone manufactured as per Example 1 (0.17 g, 0.83 mmol, 2.5 equivalent) was dissolved in dry acetonitrile, then added dropwise to the acetonitrile solution (30 ml) of 2,11-diaza[3.3](2,6)-pyridinophane-7,15-dimethoxi (0.10 g, 0.33 mmol, 1 equivalent) and K$_2$CO$_3$ (0.14 g, 0.99 mmol, 3 equivalent) at room temperature within 30 minutes (the diOMe-BP2AM macrocycle was prepared according to the following literature description: F. Banse, R. Carina, M. Delroisse, J.-J. Girerd, R. Hage, J. A. Simaan, D. Tetard, WO 1999065905 A1 Number of patent submission: PCT/GB1999/001850 patent). Then the reaction mixture was refluxed in N$_2$ atmosphere for 24 hours. After 24 hours, K$_2$CO$_3$ was filtered from the hot solution, and the mother liquor was evaporated at reduced pressure. The obtained crude product was purified with HPLC (Luna 10u-Prep C18(2) 100A (250×21.20 mm; 10 m) column), ACN:H$_2$O/TFA was applied as eluent [ACN: acetonitrile; TFA: trifluoroacetic acid]. TFA was contained only in water in 0.005 M concentration. Yield: 0.09 g (49%).

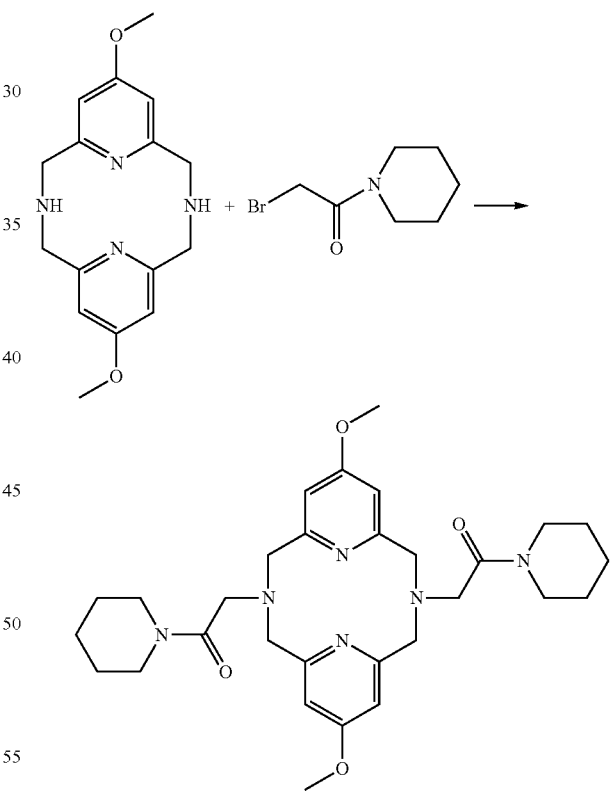

$^1$H NMR [360 MHz, D$_2$O] δ 1.54 (12H, m, (6 pcs CH$_2$)), 3.29 (4H, s, (2 pcs CH$_2$)) 3.44 (8H, m, (4 pcs CH$_2$)) 3.8-4.3 (8H, m, (4 pcs CH$_2$)), 4.12 (6H, s, 2 pcs CH$_3$), 6.68 (4H, s, (CH) aromatic);

$^{13}$C NMR [100 MHz, D$_2$O] δ 24.1 (2 pcs CH$_2$); 25.3 (2 pcs CH$_2$); 25.6 (2 pcs CH$_2$); 44.1 (4 pcs CH$_2$); 56.6 (2 pcs CH$_3$); 58.6 (2 pcs CH$_2$); 61.6 (4 pcs CH$_2$); 110.1 (4 pcs CH aromatic); 153.2 (4 pcs C aromatic); 157.2 (2 pcs C(OCH$_3$) aromatic); 172.3 (2 pcs C(=O));

EXAMPLE 6

Synthesis of BP2AM$^{Pro}$ a.) Tert-butyl 1-(2-bromoacetyl)pyrrolidine-2-carboxylate Bromoacetyl bromide (1.44 g, 7.2 mmol, 0.63 ml, 1.5 equivalent), dry CH$_2$Cl$_2$ (30 ml) and K$_3$PO$_4$ (2.55 g, 12.0 mmol, 2.5 equ.) was mixed in a flask of 250 ml and stirred under N$_2$ atmosphere. D-proline tert-butyl ester hydrochloride (1.00 g, 4.8 mmol, 1.0 equivalent) was dissolved in dry CH$_2$Cl$_2$ (20 ml) and was added dropwise to dichloromethane solution of bromoacetyl bromide at 0° C. in 30 minutes, then the reaction mixture was stirred for additional 12 hours at room temperature under N$_2$ atmosphere before the aqueous HCl solution (0.5 M, 20 ml) was added to the reaction mixture. After the addition of HCl solution, the reaction mixture was stirred for additional 5 minutes, then the two phases were separated using a separatory funnel. The aqueous phase was washed with CH$_2$Cl$_2$ (1×10 ml) and then the unified organic phases were washed with KHCO$_3$ solution (2×20 ml, 10 m/m %) and saturated NaCl solution (1×20 ml). The organic phase was dried with MgSO$_4$, then dichloromethane was evaporated at reduced pressure, and the crude product was stored at −20° C. until further use. Yield: 1.05 g (75%).

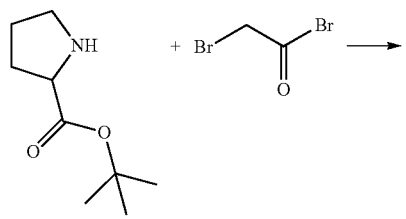

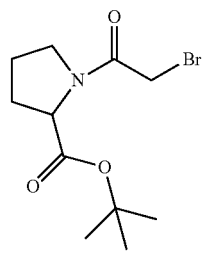

$^1$H NMR [360 MHz, CDCl$_3$] δ 1.60 (9H, s, (CH$_3$)), 2.15 (2H, m, (CH$_2$) ring), 2.43 (2H, m, (CH$_2$)ring), 3.72 (2H, m, (CH$_2$) ring), 4.00 (2H, s, (CH$_2$)), 4.55 (1H, m, (CH) ring);
$^{13}$C NMR [100 MHz, CDCl$_3$] δ 25.0 CH$_2$ ring; 27.0 CH$_2$Br; 28.0 (3C CH$_3$); 29.2 CH$_2$ ring; 47.5 CH$_2$ ring; 60.2 CH ring; 81.8 CH t-butyl; 165.2 C(=O); 170.9 C(=O);

b.) BP2AM$^{Pro}$ Synthesis

The tert-butyl 1-(2-bromoacetyl)pyrrolidine-2-carboxylate obtained as described above (0.31 g, 1.05 mmol, 2.5 equivalent) was dissolved in dry acetonitrile (20 ml) and added dropwise to the acetonitrile solution of 2,11-diaza [3.3](2,6)-pyridinophane (0.10 g, 0.42 mmol, 1 equivalent) and K$_2$CO$_3$ (0.17 g, 1.26 mmol, 3 equivalent) at room temperature within 30 minutes. Then the reaction mixture was refluxed in N$_2$ atmosphere for 24 hours. After 24 hours, K$_2$CO$_3$ was filtered from the hot solution, and acetonitrile was evaporated at reduced pressure. The obtained yellowish oil was dissolved in CH$_2$Cl$_2$ (10 ml), then trifluoroacetic acid is added to it (0.20 ml, 6 equivalent) and the reaction mixture was refluxed for 24 hours. The obtained crude product was purified with HPLC (Luna 10u-Prep C18(2) 100A (250× 21.20 mm; 10 μm) column), ACN:H$_2$O/TFA was applied as eluent [ACN: acetonitrile; TFA: trifluoroacetic acid]. TFA was contained only in water in 0.005 M concentration. Yield: 0.13 g (57%).

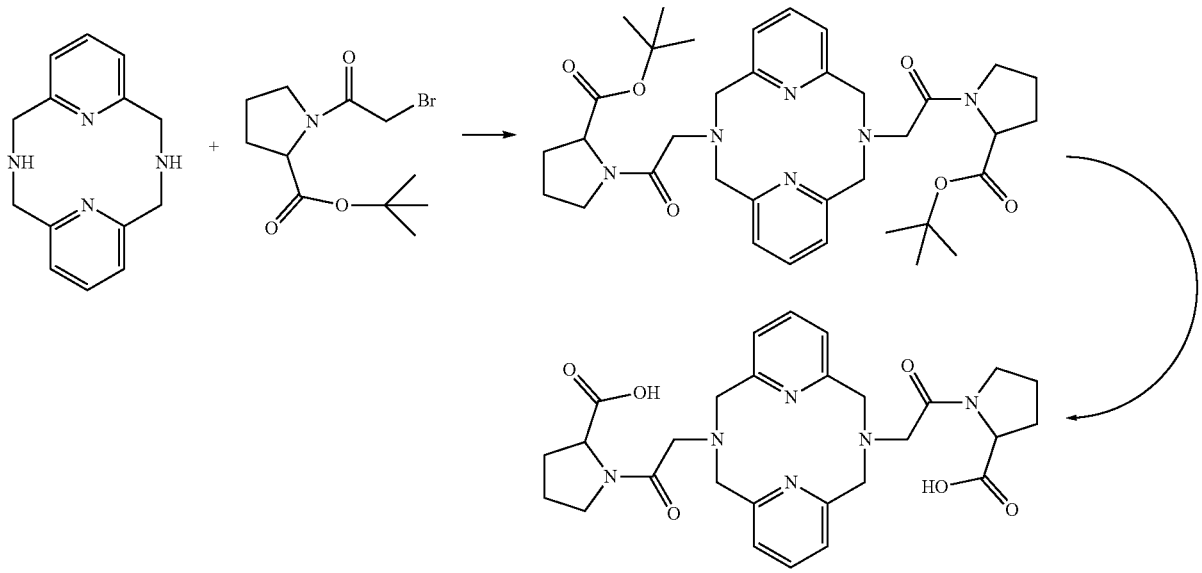

$^1$H NMR [360 MHz, D$_2$O] δ 2.1 (8H, m, (CH$_2$)), 2.34 (4H, m, (CH$_2$)), 4.48 (4H, m, (CH$_2$)), 4.55 (2H, m, (CH)), 4.61 (8H, s, (CH$_2$)), 7.35 (4H, d, (CH) aromatic), 7.88 (2H, t, (CH) aromatic);

$^{13}$C NMR [100 MHz, D$_2$O] δ 22.6 2 pcs CH$_2$; 29.0 (2 pcs CH$_2$); 46.1 (2 pcs CH$_2$); 54.5 (2 pcs CH$_2$); 59.1 (4 pcs CH$_2$); 61.2 (2 pcs CH); 121.3 (4 pcs CH aromatic); 136.8 (2 pcs CH aromatic); 156.2 (4 pcs C aromatic); 167.9 (2 pcs C(=O)); 175.2 (2 pcs C (COOH));

MS (ESI) m/z 551.46 (M+H)$^+$ 100%; 573.500 (M+Na)$^+$ 10%;

IR: 1729, 1654 cm$^{-1}$ (>C=O); 2163,1996 (aromatic >C=C) és 1147 cm$^{-1}$ (≥C—O—CS≤;

EXAMPLE 7

Synthesis of BP2AM$^{Sar}$ a.) N-(bromoacetyl)sarcosine tert-butyl ester

Bromoacetyl bromide (3.56 g, 17.6 mmol, 1.55 ml, 1.5 equivalent), dry CH$_2$Cl$_2$ (50 ml) and K$_3$PO$_4$ (6.41 g, 30.2 mmol, 2.5 equ.) was mixed in a flask of 250 ml under N$_2$ atmosphere. Sarcosine tert-butyl ester (1.7 g, 11.7 mmol, 1.0 equivalent) was dissolved in dry CH$_2$Cl$_2$ (20 ml) and was added dropwise to dichloromethane solution of bromoacetyl bromide at 0° C. in 30 minutes, then the reaction mixture was stirred for additional 12 hours at room temperature under N$_2$ atmosphere before the aqueous HCl solution (0.5 M, 30 mil) was added to the reaction mixture. After the addition of HCl solution, the reaction mixture was stirred for additional 5 minutes, then the two phases were separated using a separatory funnel. The aqueous phase was washed with CH$_2$Cl$_2$ (1×15 ml) and then the unified organic phases were washed with KHCO$_3$ solution (2×30 ml, 10 m/m %) and saturated NaCl solution (1×30 ml). The organic phase was dried with MgSO$_4$, then dichloromethane was evaporated at reduced pressure, and the crude product was stored at −20° C. until further use. Yield: 2.01 g (65%).

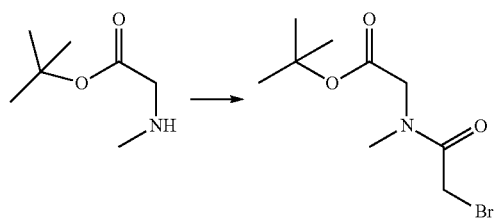

$^1$H NMR [360 MHz, CDCl$_3$] δ 1.6 (9H, s, CH$_3$) 2.8 (3H, s, CH$_3$), 4.01 (2H, s, CH$_2$), 4.4 (2H, s, CH$_2$)

b). Synthesis of BP2AM$^{Sar}$

The N-(bromoacetyl)sarcosine tert-butyl ester obtained as described above (0.28 g, 1.05 mmol, 2.5 equivalent) was dissolved in dry acetonitrile (20 ml) and added dropwise to the acetonitrile solution of 2,11-diaza[3.3](2,6)-pyridinophane (0.10 g, 0.42 mmol, 1 equivalent) and K$_2$CO$_3$ (0.17 g, 1.26 mmol, 3 equivalent) at room temperature within 30 minutes. Then the reaction mixture was refluxed in N2 atmosphere for 24 hours. After 24 hours, K$_2$CO$_3$ was filtered from the hot solution, and acetonitrile was evaporated at reduced pressure. The obtained yellowish oil was dissolved in CH$_2$Cl$_2$ (10 ml), then trifluoroacetic acid is added to it (0.25 ml, 6 equivalent) and the reaction mixture was refluxed for 24 hours. The obtained crude product was purified with HPLC (Luna 10u-Prep C18(2) 100A (250× 21.20 mm; 10 μm) column), ACN:H$_2$O/TFA was applied as eluent [ACN: acetonitrile; TFA: trifluoroacetic acid]. TFA was contained only in water in 0.005 M concentration. Yield: 0.12 g (57%). $^1$H NMR [360 MHz, D$_2$O] δ 7.91 (2H, t, aromatic), 7.10 (4H, d, aromatic) 4.96 (4H, s, CH$_2$) 4.11 (8H, s, CH$_2$) 3.67 (6H, s, CH$_3$) 3.49 (4H, CH$_2$).

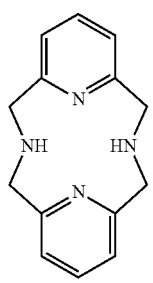

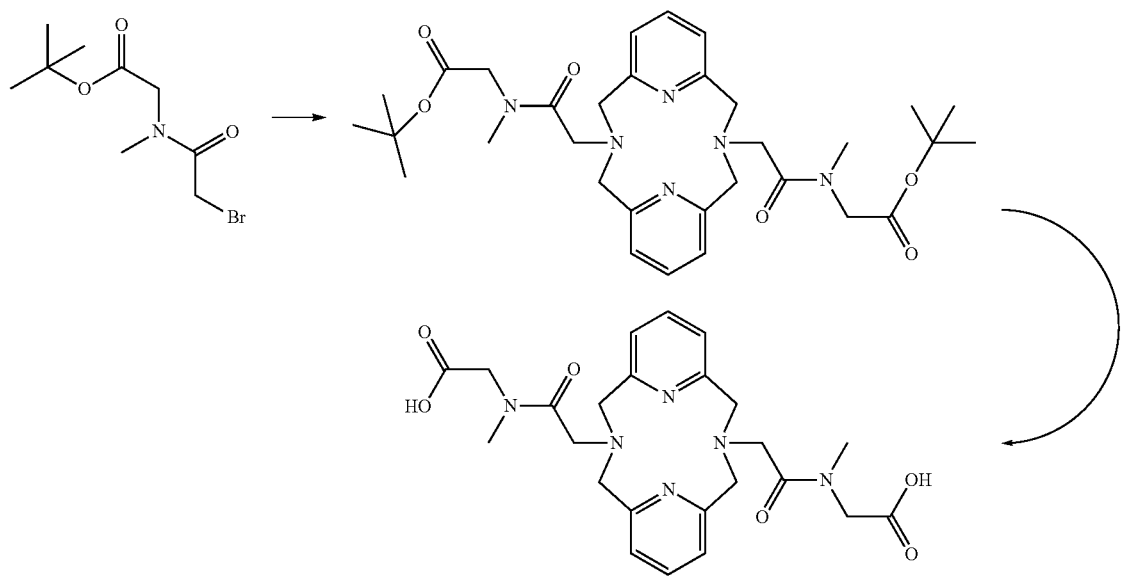

EXAMPLE 8

Synthesis of BP2AM$^{PypCOOH}$ a.) N-(bromoacetyl)piperidine-4-carboxylic acid tert-butyl ester Bromoacetyl bromide (3.56 g, 17.6 mmol, 1.55 ml, 1.5 equivalent), dry $CH_2Cl_2$ (50 ml) and $K_3PO_4$ (6.41 g, 30.2 mmol, 2.5 equivalent) was mixed in a flask of 250 ml under $N_2$ atmosphere. Piperidine tert-butyl ester (2.2 g, 11.7 mmol, 1.0 equivalent) was dissolved in dry $CH_2Cl_2$ (20 ml) and was added dropwise to dichloromethane solution of bromoacetyl bromide at 0° C. in 30 minutes, then the reaction mixture was stirred for additional 12 hours at room temperature under $N_2$ atmosphere before the aqueous HCl solution (0.5 M, 30 ml) was added to the reaction mixture. After the addition of HCl solution, the reaction mixture was stirred for additional 5 minutes, then the two phases were separated using a separatory funnel. The aqueous phase was washed with $CH_2Cl_2$ (1×15 ml) and then the unified organic phases were washed with $KHCO_3$ solution (2×30 ml, 10 m/m %) and saturated NaCl solution (1×30 ml). The organic phase was dried with $MgSO_4$, then dichloromethane was evaporated at reduced pressure, and the crude product was stored at −20° C. until further use. Yield: 2.1 g (59%).

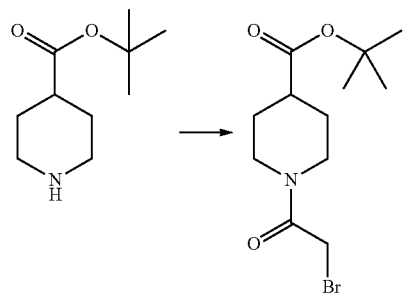 [SMILES: CC(C)(C)OC(=O)C1CCNCC1 ; CC(C)(C)OC(=O)C1CCN(C(=O)CBr)CC1]

$^1$H NMR [360 MHz, $CDCl_3$] δ 1.50 (9H, s, $CH_3$) 2.50 (1H, s, CH), 4.01 (2H, s, ($CH_2$), 3.5-1.6 (8H, m, $CH_2$), 4.31 (2H, s, $CH_2$)

b.) Synthesis of BP2AM$^{PypCOOH}$

The N-(bromoacetyl)piperidine tert-butyl ester obtained as described above (0.32 g, 1.05 mmol, 2.5 equivalent) was dissolved in dry acetonitrile (20 ml) and added dropwise to the acetonitrile solution of 2,11-diaza[3.3](2,6)-pyridinophane (0.10 g, 0.42 mmol, 1 equivalent) and $K_2CO_3$ (0.17 g, 1.26 mmol, 3 equivalent) at room temperature within 30 minutes. Then the reaction mixture was refluxed in $N_2$ atmosphere for 24 hours. After 24 hours, $K_2CO_3$ was filtered from the hot solution, and acetonitrile was evaporated at reduced pressure. The obtained yellowish oil was dissolved in CH$_2$Cl$_2$ (10 ml), then trifluoroacetic acid is added to it (0.25 ml, 6 equivalent) and the reaction mixture was refluxed for 24 hours. The obtained crude product was purified with HPLC (Luna 10u-Prep C18(2) 100A (250× 21.20 mm; 10 μm) column), ACN:H$_2$O/TFA was applied as eluent [ACN: acetonitrile; TFA: trifluoroacetic acid]. TFA was contained only in water in 0.005 M concentration. Yield: 0.14 g (60%). 1H NMR [360 MHz, D$_2$O] δ 7.91 (2H, t, aromatic), 7.33 (4H, d, aromatic) 4.10 (8H, s, CH$_2$) 3.51-3.18 (8H, m, CH$_2$) 3.40 (4H, CH$_2$) 2.45 (2H, m, CH) 1.91-1.50 (8H, m, CH$_2$)

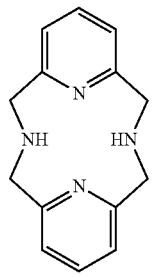

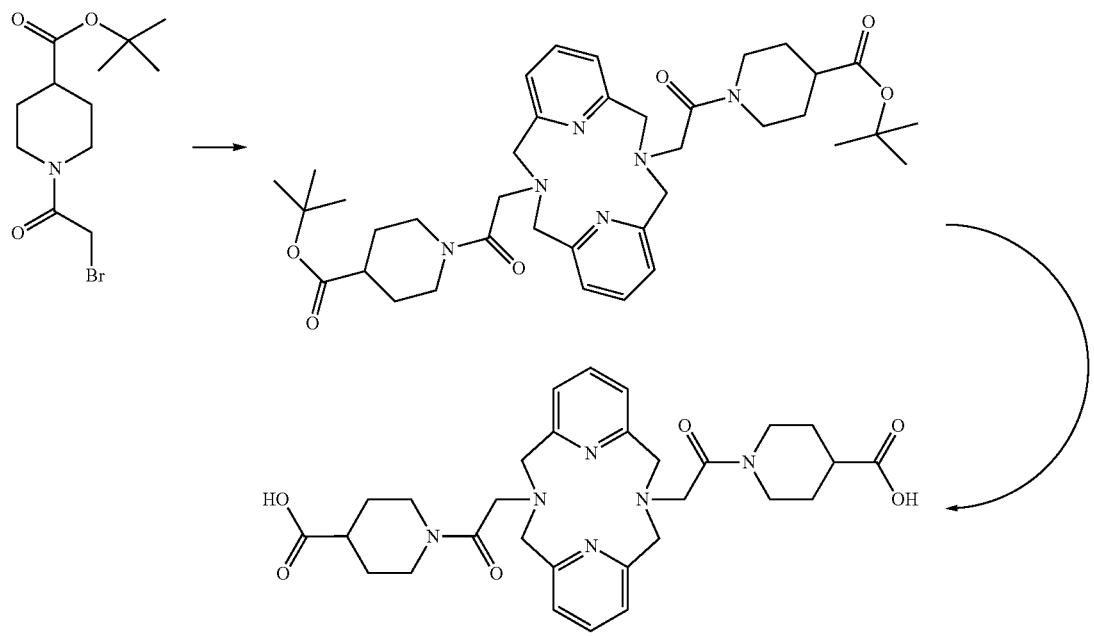

EXAMPLE 9

Synthesis of BP2AM$^{PypCOONHS}$

The BP2AM$^{PypCOOH}$ (0.20 g, 0.35 mmol, 1.0 equivalent) obtained as described above was dissolved in dry DMF, then DCC (0.15 g, 0.70 mmol, 2 equ.) was added at room temperature and the reaction mixture was stirred at room temperature for 2 hours. Then NHS (N-Hydroxysuccinimide) (0.08 g, 0.70 mmol, 2 equ.) was added and the reaction mixture was stirred for additional 20 hours. When the reaction time was elapsed, the precipitate was filtered, and the filtrate was evaporated at reduced pressure. The obtained crude product was purified with HPLC (Luna 10u-Prep C18(2) 100A (250×21.20 mm; 10 μm) column), ACN:H$_2$O/TFA was applied as eluent [ACN: acetonitrile; TFA: trifluoroacetic acid]. TFA was contained only in water in 0.005 M concentration. Yield: 0.13 g (48%).

$^1$H NMR [360 MHz, D$_2$O] δ 7.9 (2H, t, aromatic), 7.30 (4H, d, aromatic) 4.11 (8H, s, CH$_2$) 3.61-3.17 (8H, m, CH$_2$) 3.49 (4H, CH$_2$) 2.55 (8H, s, CH$_2$) 2.44 (2H, m, CH) 1.96-1.50 (8H, m, CH$_2$).

stirred for additional 5 minutes, then the two phases were separated using a separatory funnel. The aqueous phase was washed with CH$_2$Cl$_2$ (1×15 ml) and then the unified organic phases were washed with KHCO$_3$ solution (2×30 ml, 10 m/m %) and saturated NaCl solution (1×30 mil). The organic phase was dried with MgSO$_4$, then dichloromethane was evaporated at reduced pressure, and the crude product was stored at −20° C. until further use. Yield: 1.85 g (67%).

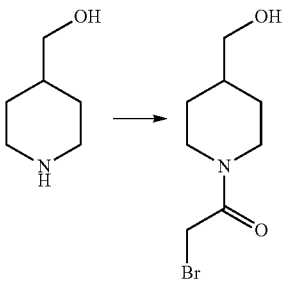 [SMILES: OCC1CCNCC1 ; O=C(CBr)N1CCC(CO)CC1]

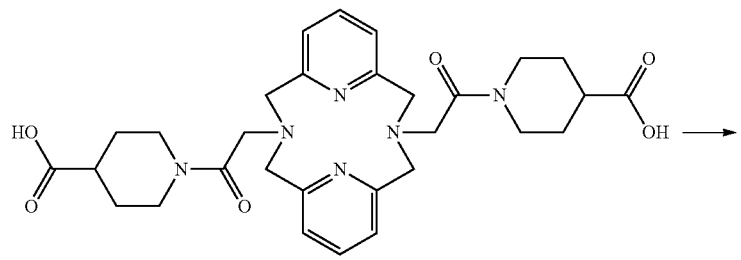

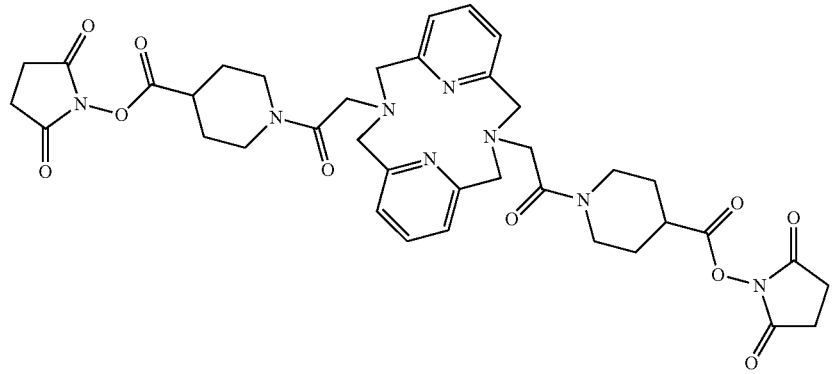

EXAMPLE 10

Synthesis of BP2AM$^{PypCH2OH}$ a.) N-bromoacetyl-4-hydroxymethyl piperidine Bromoacetyl bromide (3.56 g, 17.6 mmol, 1.55 ml, 1.5 equivalent), dry CH$_2$Cl$_2$ (50 ml) and K$_3$PO$_4$ (6.41 g, 30.2 mmol, 2.5 equ.) was mixed in a flask of 250 ml under N$_2$ atmosphere. 4-hydroxymethyl piperidine (1.34 g, 11.7 mmol, 1.0 equivalent) was dissolved in dry CH$_2$Cl$_2$ (20 ml) and was added dropwise to dichloromethane solution of bromoacetyl bromide at 0° C. in 30 minutes, then the reaction mixture was stirred for additional 12 hours at room temperature under N$_2$ atmosphere before the aqueous HCl solution (0.5 M, 30 ml) was added to the reaction mixture. After the addition of HCl solution, the reaction mixture was $^1$H NMR [360 MHz, CDCl$_3$] δ 1.61 (1H, m, CH) 1.71-1.30 (8H, m, CH$_2$), 3.52 (2H, m, (CH$_2$), 4.21 (2H, s, CH$_2$).

b.) Synthesis of BP2AM$^{PypCH2OH}$

The N-bromoacetyl-4-hydroymethyl piperidine obtained as described above (0.25 g, 1.05 mmol, 2.5 equivalent) was dissolved in dry acetonitrile and added dropwise to the acetonitrile solution (30 ml) of 2,11-diaza[3.3](2,6)-pyridinophane (0.10 g, 0.42 mmol, 1 equivalent) and K$_2$CO$_3$ (0.17 g, 1.26 mmol, 3 equivalent) at room temperature within 30 minutes. Then the reaction mixture was refluxed in N$_2$ atmosphere for 24 hours. After 24 hours, K$_2$CO$_3$ was filtered from the hot solution, and acetonitrile was evaporated at reduced pressure. The obtained crude product was purified with HPLC (Luna 10u-Prep C18(2) 100A (250×21.20 mm; 10 μm) column), ACN:H$_2$O/TFA was applied as eluent

[ACN: acetonitrile; TFA: trifluoroacetic acid]. TFA was contained only in water in 0.005 M concentration. Yield: 0.15 g (66%).

$^1$H NMR [360 MHz, D$_2$O] δ 7.92 (2H, t, aromatic), 7.34 (4H, d, aromatic) 4.00 (8H, s, CH$_2$) 3.70 (4H, d, CH$_2$) 3.51-3.24 (8H, m, CH$_2$) 3.39 (4H, CH$_2$) 1.68 (2H, m, piperidin CH) 1.69-1.24 (8H, m, CH$_2$)

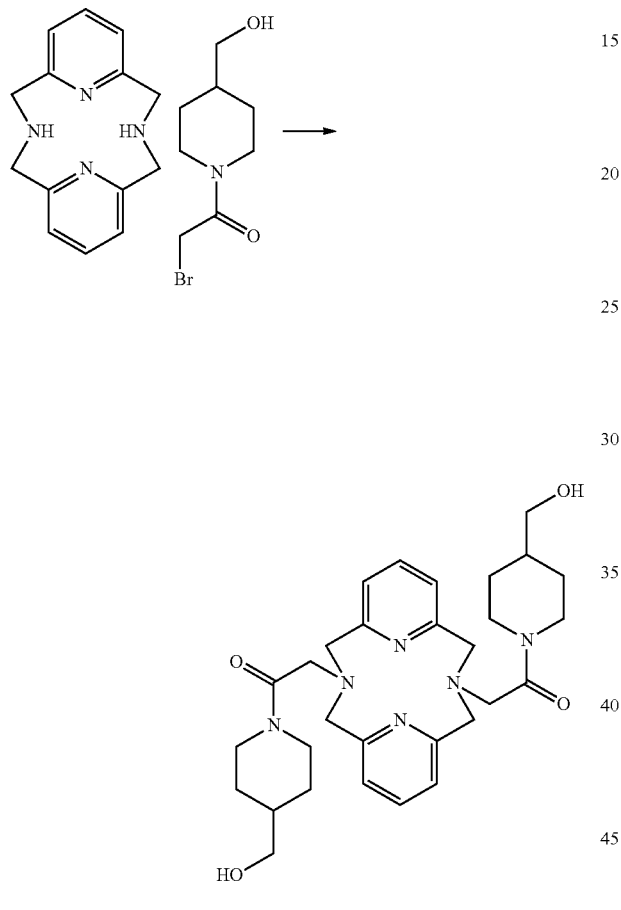

EXAMPLE 11

Synthesis of BP2AM$^{PypBn}$ a.) N-bromoacetyl-4-benzylpiperidine

Bromoacetyl bromide (3.56 g, 17.6 mmol, 1.55 ml, 1.5 equivalent), dry CH$_2$Cl$_2$ (50 ml) and K$_3$PO$_4$ (6.41 g, 30.2 mmol, 2.5 equ.) was mixed in a flask of 250 ml under N$_2$ atmosphere. 4-benzylpiperidine (2.05 g, 11.7 mmol, 1.0 equivalent) was dissolved in dry CH$_2$Cl$_2$ (20 ml) and was added dropwise to dichloromethane solution of bromoacetyl bromide at 0° C. in 30 minutes, then the reaction mixture was stirred for additional 12 hours at room temperature under N$_2$ atmosphere before the aqueous HCl solution (0.5 M, 30 ml) was added to the reaction mixture. After the addition of HCl solution, the reaction mixture was stirred for additional 5 minutes, then the two phases were separated using a separatory funnel. The aqueous phase was washed with CH$_2$Cl$_2$ (1×15 ml) and then the unified organic phases were washed with KHCO$_3$ solution (2×30 ml, 10 m/m %) and saturated NaCl solution (1×30 ml). The organic phase was dried with MgSO$_4$, then dichloromethane was evaporated at reduced pressure, and the crude product was stored at −20° C. until further use. Yield: 1.85 g (67%).

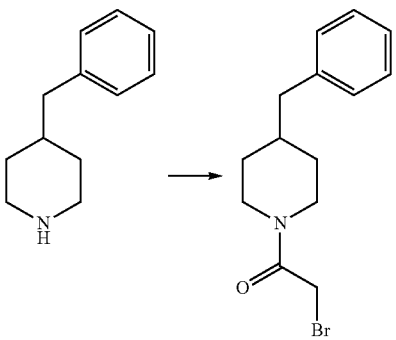 [SMILES: c1ccc(CC2CCNCC2)cc1 ; O=C(CBr)N1CCC(Cc2ccccc2)CC1]

$^1$H NMR [360 MHz, CDCl$_3$] δ 1.91 (1H, m, CH) 1.69-1.24 (8H, m, CH$_2$) 2.66 (2H, m, CH$_2$) 4.23 (2H, s, (CH$_2$), 7.05-7.33 (5H, m, aromatic)

b.) Synthesis of BP2AM$^{PypBn}$

The N-bromoacetyl-4-benzylpiperidine obtained as described above (0.31 g, 1.05 mmol, 2.5 equivalent) was dissolved in dry acetonitrile and added dropwise to the acetonitrile solution (30 ml) of 2,11-diaza[3.3](2,6)-pyridinophane (0.10 g, 0.42 mmol, 1 equivalent) and K$_2$CO$_3$ (0.17 g, 1.26 mmol, 3 equivalent) at room temperature within 30 minutes. Then the reaction mixture was refluxed in N$_2$ atmosphere for 24 hours. After 24 hours, K$_2$CO$_3$ was filtered from the hot solution, and acetonitrile was evaporated at reduced pressure. The obtained crude product was purified with HPLC (Luna 10u-Prep C18(2) 100A (250×21.20 mm; 10 μm) column), ACN:H$_2$O/TFA was applied as eluent [ACN: acetonitrile; TFA: trifluoroacetic acid]. TFA was contained only in water in 0.005 M concentration. Yield: 0.19 g (66%).

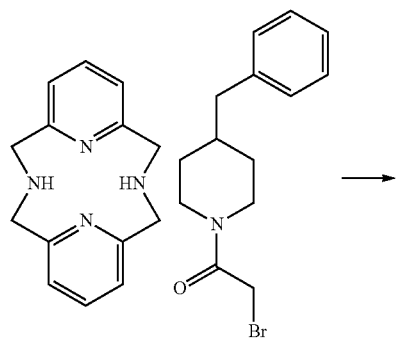

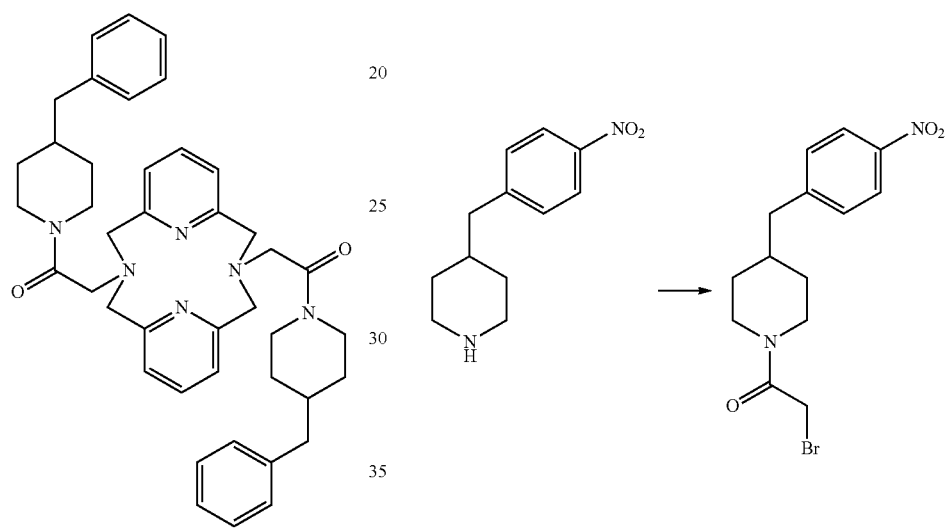

¹H NMR [360 MHz, D2O] δ 7.92 (2H, t, aromatic), 7.51 (4H, m, aromatic) 7.33-7.17 (6H, m, aromatic) 7.41 (4H, d, aromatic) 4.15 (8H, s, CH₂) 3.55-3.11 (8H, m, CH₂) 3.34 (4H, m, CH₂) 2.66 (4H, d, CH₂) 1.92 (2H, m, CH) 1.70-1.36 (8H, m, CH₂)

EXAMPLE 12

Synthesis of BP2AMP$^{PypBnNO2}$ a.) N-bromoacetyl-4-(4'-nitrobenzyl)piperidine

Bromoacetyl bromide (3.56 g, 17.6 mmol, 1.55 ml, 1.5 equivalent), dry CH₂Cl₂ (50 ml) and K₃PO₄ (6.41 g, 30.2 mmol, 2.5 equ.) was mixed in a flask of 250 ml under N₂ atmosphere. 4-(4'-nitrobenzyl)piperidine (2.57 g, 11.7 mmol, 1.0 equivalent) was dissolved in dry CH₂Cl₂ (20 ml) and was added dropwise to dichloromethane solution of bromoacetyl bromide at 0° C. in 30 minutes, then the reaction mixture was stirred for additional 12 hours at room temperature under N₂ atmosphere before the aqueous HCl solution (0.5 M, 30 ml) was added to the reaction mixture. After the addition of HCl solution, the reaction mixture was stirred for additional 5 minutes, then the two phases were separated using a separatory funnel. The aqueous phase was washed with CH₂Cl₂ (1×15 ml) and then the unified organic phases were washed with KHCO₃ solution (2×30 ml, 10 m/m %) and saturated NaCl solution (1×30 ml). The organic phase was dried with MgSO₄, then dichloromethane was evaporated at reduced pressure, and the crude product was stored at −20° C. until further use. Yield: 2.43 g (61%).

¹H NMR [360 MHz, CDCl₃] δ 1.90 (1H, m, CH) 1.62-1.33 (8H, m, CH₂) 2.56 (2H, m, CH₂) 4.21 (2H, s, (CH₂), 7.40-8.3 (4H, m, aromatic)

b.) Synthesis of BP2AM$^{PypBnNO2}$

The N-bromoacetyl-4-(4'-nitrobenzyl)piperidine obtained as described above (0.36 g, 1.05 mmol, 2.5 equivalent)) was dissolved in dry acetonitrile and added dropwise to the acetonitrile solution (30 ml) of 2,11-diaza[3.3](2,6)-pyridinophane (0.10 g, 0.42 mmol, 1 equivalent) and K₂CO₃ (0.17 g, 1.26 mmol, 3 equivalent) at room temperature within 30 minutes. Then the reaction mixture was refluxed in N₂ atmosphere for 24 hours. After 24 hours, K₂CO₃ was filtered from the hot solution, and acetonitrile was evaporated at reduced pressure. The obtained crude product was purified with HPLC (Luna 10u-Prep C18(2) 100A (250×21.20 mm; 10 μm) column), ACN:H₂O/TFA was applied as eluent [ACN: acetonitrile; TFA: trifluoroacetic acid]. TFA was contained only in water in 0.005 M concentration. Yield: 0.22 g (70%).

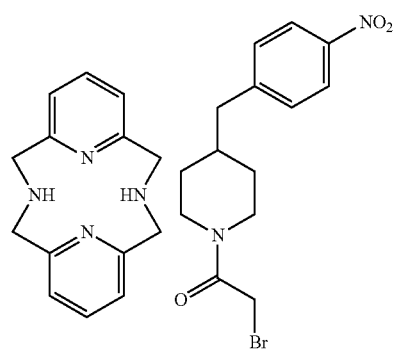 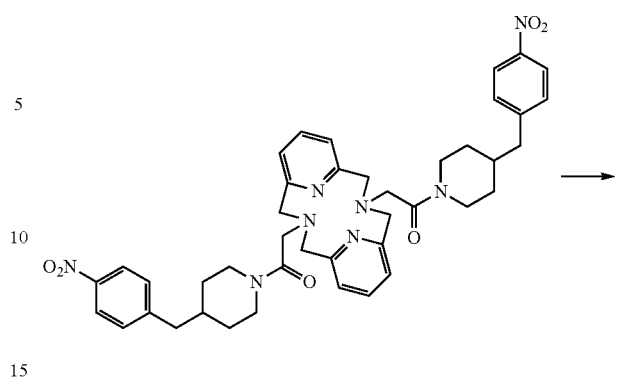

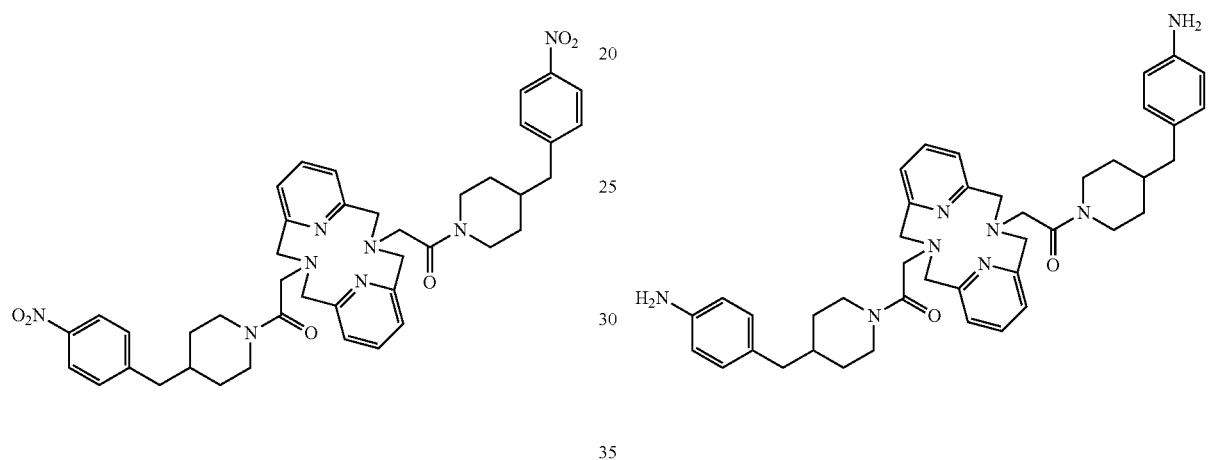

¹H NMR [360 MHz, D2O] δ 8.41 (4H, m, aromatic) 7.95 (2H, t, aromatic), 7.75 (4H, m, aromatic) 7.32 (4H, d, aromatic) 3.84 (8H, s, CH₂) 3.49-3.19 (8H, m, CH₂) 3.49 (4H, CH₂) 2.44 (4H, d, CH₂) 1.98 (2H, m, CH) 1.33-1.24 (8H, m, CH₂)

c.) Synthesis of BP2A$^{PypBnNH}$

The above obtained BP2A$^{PypBnNO2}$ (0.4 g, 0.26 mmol) was dissolved in dry methanol, 0.04 g Pd-carbon catalyst was added, and then the mixture was reduced under 1 bar hydrogen pressure at room temperature for 2 hours. The catalyst was removed by filtration, the filtrate was evaporated at reduced pressure. Yield: 0.15 g (83%). ¹H NMR [360 MHz, D₂O] δ 8.41 (4H, m, aromatic) 7.95 (2H, t, aromatic), 7.75 (4H, m, aromatic) 7.32 (4H, d, aromatic) 3.84 (8H, s, CH₂) 3.49-3.19 (8H, m, CH₂) 3.49 (4H, CH₂) 2.44 (4H, d, CH₂) 1.98 (2H, m, CH) 1.33-1.24 (8H, m, CH₂)

EXAMPLE 13

Efficacy Data

During the physico-chemical studies of BP2AM$^{Pyp}$ and BP2AM$^{Pro}$ compounds prepared according to Example 1 and 2, their protonation constants, as well as equilibrium behaviour and kinetic inertness of their Mn(II) complexes was studied in detail, and the characteristic relaxivity values of the complexes were determined in the presence and absence of HSA (Human Serum Albumin), at 25 and 37° C. and physiological pH. All studies were performed in the presence of 0.15 M NaCl, the same concentration as that of the electrolyte under physiological conditions.

The results of equilibrium study are summarized in Table 1, in addition to the protonation constants, total basicity of ligands and stability constants of their Mn(II) complexes, the pMn value calculated for complexes are also represented in the table.

TABLE 1

Protonation constants and total basicity of the studied ligands, stability constants of their Mn(II) complexes and calculated pMn values (25° C., 0.15M NaCl).

|  | $logK_1$ | $logK_2$ | $logK_3$ | $logK_4$ | $\Sigma logK_i^H$ | $logK_{MnL}$ | pMn |
|---|---|---|---|---|---|---|---|
| BP2AM$^{Pyp}$ | 9.57(2) | 2.99(2) | — | — | 12.56 | 13.58(1) | 8.19 |
| BP2AM$^{Pro}$ | 8.83(1) | 3.89(2) | 3.05(2) | 2.39(2) | 18.16 | 11.47(5) | 7.51 | pMn values were calculated by using the equilibrium constants at pH = 7.4 and cMn = cL = $10^{-5}$ M Based on the pMn values presented in Table 1 (calculated using the equilibrium constants at pH=7.4 and cMn=cL=10⁻⁵ M), it can be concluded that the studied Mn(II) complexes are formed in 100% at physiological pH, which is an essential aspect of the practical use.

An important parameter of using Mn(II) containing contrast agents in vivo is the low kinetic reactivity of the complex. The kinetic reactivity is generally tested with metal ion exchange reactions, where the replacing metal ion is Zn(II) or Cu(II) in most of the cases. The application of Cu(II) is advantageous for more reasons, in one hand the complexes with ligands are of great thermodynamic stability, so relatively small excess of Cu(II) ion leads to complete replacement, on the other hand molar absorbance values of Cu(II) complexes both in UV and visible range are sufficiently high to enable spectrophotometric method for examinations even at low concentrations. Moreover, the endogenic character of the Cu(II) ion provides additional information on in vivo processes. Replacement reactions were executed with at least 10-fold excess Cu(II) ion concentration to ensure pseudo-first order conditions.

Dissociation reactions of Mn(II) complexes may take place in several pathways as represented below.

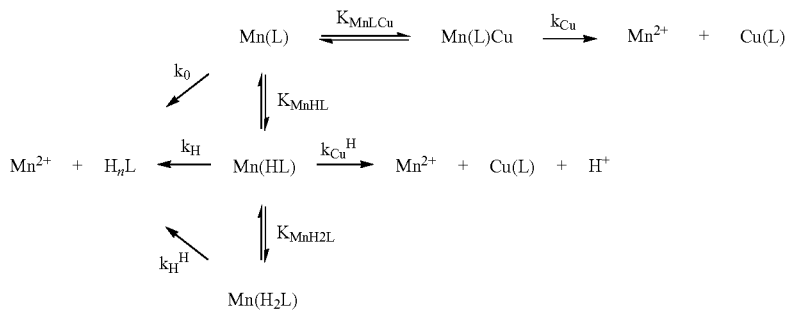

The $k_0$, $k_H$, $k_H^H$, $k_{Cu}$ and $k_{Cu}^H$, rate constants indicate the spontaneous, proton associated, metal assisted and proton-metal assisted (when the replacing metal ion attacks the protonated complex) reaction pathways of the complex. The $K_{MnHL}$, $K_{MnH_2L}$ and $K_{MnLCu}$ are stability constants of the protonated and binuclear intermediate complexes.

In case of metal complexes formed with macrocyclic ligands the above detailed mechanism involves only proton associated dissociation pathways (in some instances spontaneous dissociation may have some role), since the formation of binuclear complexes are inhibited (denticity of rigid ligands does not exceed the coordination number of the metal ion, $Mn^{2+}$). Due to this reason, replacement reactions were executed in 2.0-5.0 pH range with only 10-fold Cu(II) replacement metal ion excess.

In general the $k_{obs}$ pseudo-first order rate constants obtained in each reaction are given with the following equation, where the stability constants of each reaction pathway and that of the forming intermediate are also considered:

$$k_{obs} = \frac{k_0 + k_1[H^+] + k_2[H^+]^2 + k_3[Cu^{2+}] + k_4[Cu^{2+}][H^+]}{1 + K_{MnHL}[H^+] + K_{MnH_2L}[H^+]^2 + K_{MnLCu}[Cu^{2+}]}, \quad (1)$$

whereas $K_{MnHL}=[Mn(HL)]/[Mn(L)][H^+]$, $K_{MnH_2L}=[Mn(H_2L)]/[Mn(HL)][H^+]$, $K_{MnLCu}=[Mn(L)M]/[Mn(L)][M]$, $k_1=k_H \cdot K_{MnHL}$, $k_2=k_H^H \cdot K_{MnHL} \cdot K_{MnH_2L}$, $k_3=k_{Cu} \cdot K_{MnLCu}$ $k_4=k_{Cu}^H \cdot K_{MnHL}$ Results of the kinetic study showed that in the dissociation of $[Mn(BP2AM^{Pyp})]^{2+}$- and $[Mn(BP2AM^{Pro})]$ complexes, the proton associated dissociation (characterized with $k_1$) plays an important role. Using these rate constants the half-life ($t_{1/2}$) of $[Mn(BP2AM^{Pyp})]^{2+}$- and $[Mn(BP2AM^{Pro})]$ complexes dissociation may be calculated at physiologic pH, being $1.37 \times 10^5$ and $1.1 \times 10^4$ hours, respectively.

In order to estimate the quantity of complex decomposing in the body, it is useful to handle elimination and complex dissociation as parallel, primary reaction characterized by the (2) equation set for $Gd^{3+}$ complexes [F. K. Kálmán and G. Tircsó, Inorg. Chem., 2012, 51, 10065]:

$$[GdL]_d = \frac{k_d}{k_d + k_{ex}}[GdL]_0(1 - e^{-(k_d + k_{ex})t}) \quad (2)$$

The equation indicates that dissociation degree of the complex depends on the ration of rate constants. For the (renal) elimination of contrast agent 1.6 hour half life can be given in general, characterized by a $k_{ex}=0.433$ h⁻¹ rate constant. Using the $k_d$ values of Mn(II) complexes and the $k_{ex}$ values characteristic for elimination, one can calculate the percentile ratio of injected complex dissociated in vivo until complete elimination (12-24 hours). Calculation verified, that less than 0.8% of the complexes would dissociate before the elimination of the complex. Considering the endogenic characteristic of Mn(II) complexes and its negligible amount it cannot cause significant burden for MRI tested patients. Considering the new results, during the in vivo dissociation (37° C.) of $[Gd(DTPA)]^{2-}$ complex (Magnevist) applied in practice, 2.2% Gd(III) ion releases being 4.4-fold of the value calculated on the basis of experiments at 25° C. (0.5%). [Sarka L. et al, Chem. Eur. J., 2000, 6, 719]. Using this finding, the quantity of in vivo releasing Mn(II) for the presented Mn(II) complexes is approximately 3%. This value is better than some of those applied for Gd containing contrast agents in practice [Baranyai Z et al, Chem. Eur. J., 2015, 21, 4789]

In addition to appropriately low kinetic reactivity, complexes shall also have suitable relaxivity for the purpose of practical use (relaxivity (mM⁻¹s⁻¹): relaxation rate increase of 1 mM solution of the paramagnetic substance compared to the measured value under diamagnetic conditions [Tóth É., et. al., The Chemistry of Contrast Agents in Medical Magnetic Resonance Imaging, Chichester: John Wiley & Sons, 2001.]). Higher complex relaxivity results in higher contrast increasing effect, meaning that the same image quality is obtained by introducing less amount of complex with higher relaxivity. The relaxivity value of both complexes were determined at pH=7.4 and 25 and 37° C. in the presence and absence of HSA (Human Serum Albumin, c=0.7 mM) to better stimulate conditions of the in vivo application. Relaxivity values of the complexes are presented in Table 2. Comparing the data in Table 2 with the relaxivity values of DOTAREM ([Gd(DOTA)]$^-$ complex, $r_1$=3.83 mM$^{-1}$s$^{-1}$) and MAGNEVIST ([Gd(DTPA)]$^{2-}$ complex, $r_1$=4.02 mM$^{-1}$s$^{-1}$) [Powell, D. H., Ni Dhubhghaill, O. M., Pubanz, D. et al. (1996) J. Am. Chem. Soc., 118, 9333-9346] applied in practice under the same conditions, the Mn(II) complexes presented herein obviously have higher contrast enhancing effect.

TABLE 2

Relaxivity values (20 MHz) of the Mn$^{2+}$ complexes prepared and studied (pH = 7.4).

| Complex | T (° C.) | $r_1$ (mM$^{-1}$s$^{-1}$) | $r_1$ (mM$^{-1}$s$^{-1}$) HSA |
|---|---|---|---|
| [Mn(BP2AM$^{Pip}$)]$^{2+}$ | 25 | 4.68 | 7.94 |
|  | 37 | 3.74 | 6.32 |
| [Mn(BP2AM$^{Pro}$)] | 25 | 5.67 | 6.94 |
|  | 37 | 4.37 | 5.29 |

The invention claimed is:

1. A compound selected from:

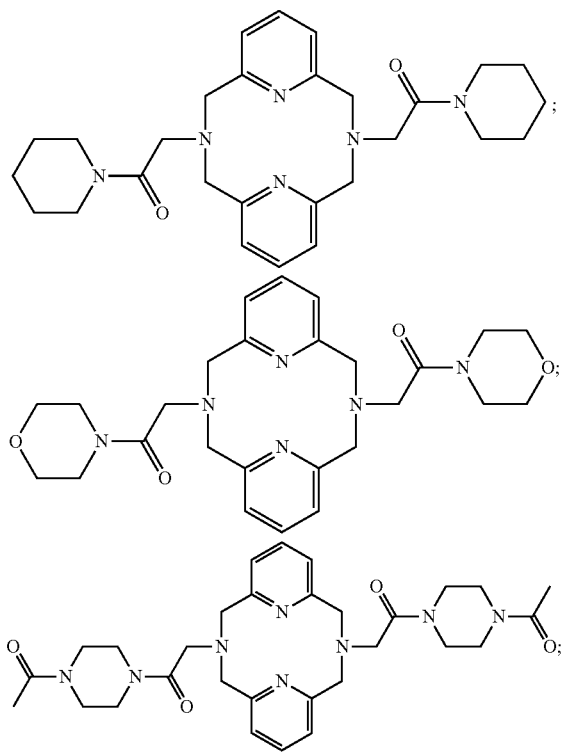

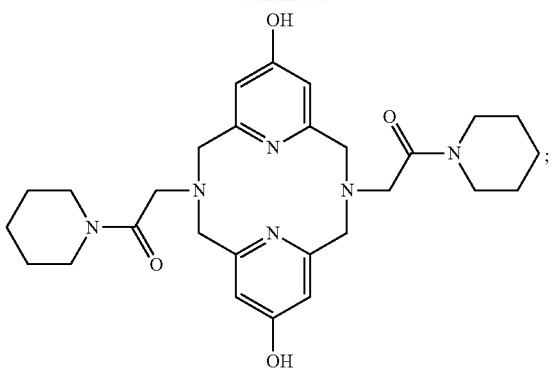

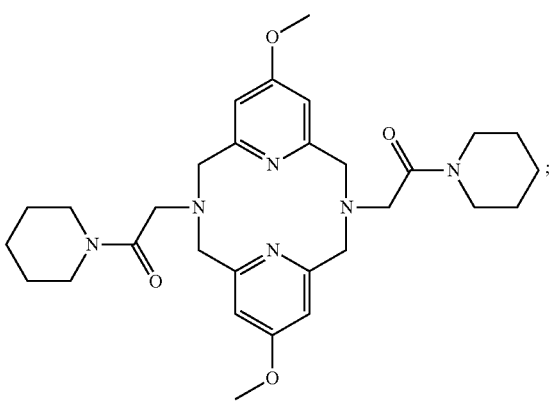

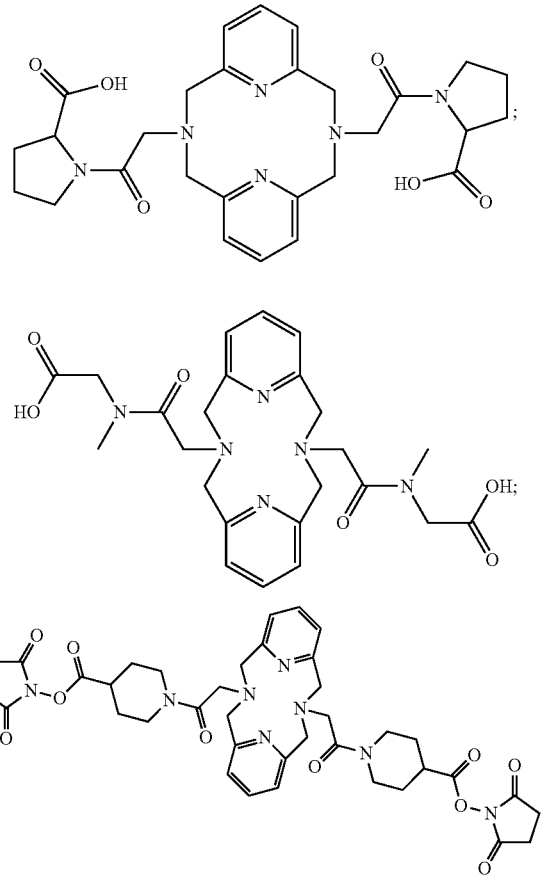

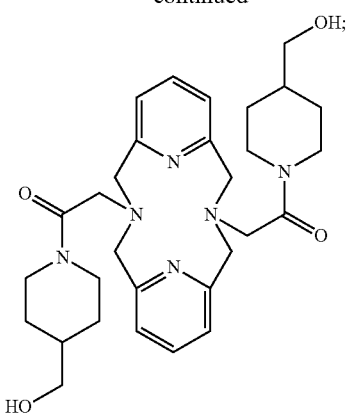

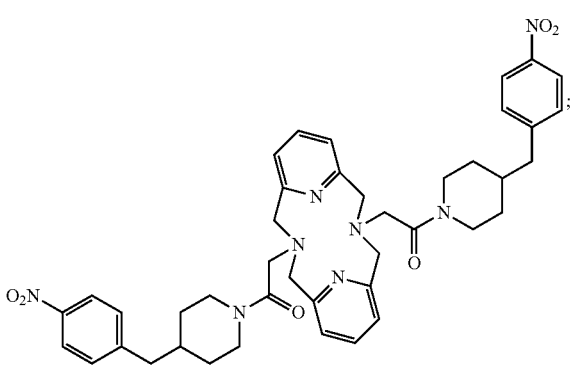

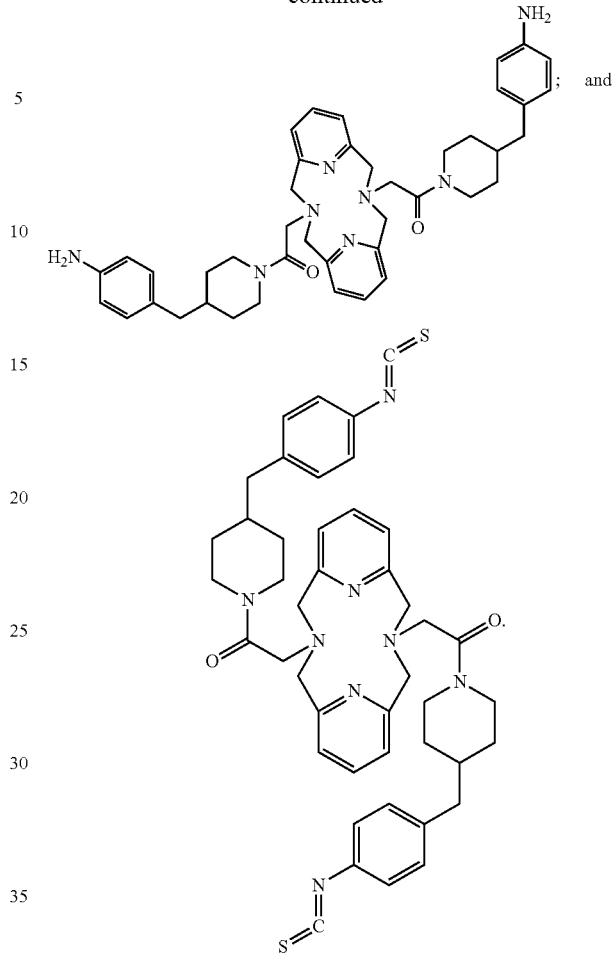

2. A complex comprising the compound of claim 1 and a metal selected from Mn(II), Fe(II), Fe(III), Co(II), and Ni(II).

3. A method of imaging, comprising:
   administering a compound according to claim 1 as a contrast agent in diagnostic imaging, and
   performing diagnostic imaging.

4. A kit for use in diagnostic imaging, comprising: a compound of claim 1.

5. A method of imaging, comprising:
   administering a complex according to claim 2 as a contrast agent in diagnostic imaging, and
   performing diagnostic imaging.

6. A kit for use in diagnostic imaging, comprising: a complex of claim 2.

* * * * *